(12) United States Patent
Takami et al.

(10) Patent No.: US 12,274,466 B2
(45) Date of Patent: Apr. 15, 2025

(54) MEDICAL DEVICE AND METHOD FOR CONTROLLING THE SAME INCLUDING DISCRIMINATING END-OF-CUT CONDITIONS BASED ON TEMPERATURE

(71) Applicant: OLYMPUS MEDICAL SYSTEMS CORP., Tokyo (JP)

(72) Inventors: Sadayoshi Takami, Hachioji (JP); Kotaro Nakamura, Sagamihara (JP); Toshifumi Katsuragi, Hachioji (JP); Gen Kato, Hachioji (JP); Shohei Moriwaki, Akishima (JP); Shunsuke Matsui, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 709 days.

(21) Appl. No.: 17/544,295

(22) Filed: Dec. 7, 2021

(65) Prior Publication Data

US 2022/0265303 A1 Aug. 25, 2022

Related U.S. Application Data

(60) Provisional application No. 63/153,548, filed on Feb. 25, 2021.

(51) Int. Cl.
*A61B 17/32* (2006.01)
*A61B 17/00* (2006.01)
*A61B 90/00* (2016.01)

(52) U.S. Cl.
CPC .......... *A61B 17/320068* (2013.01); *A61B 2017/0003* (2013.01); *A61B 2017/00084* (2013.01);

(Continued)

(58) Field of Classification Search
CPC .. A61B 17/320068; A61B 2017/00017; A61B 2017/00022; A61B 2017/00026;
(Continued)

(56) References Cited

U.S. PATENT DOCUMENTS 8,749,116 B2 6/2014 Messerly et al.
9,848,903 B2 12/2017 Tsubuku et al.
(Continued)

OTHER PUBLICATIONS

Extended European Search Report issued in corresponding European Patent Application No. 22150065.5, dated Jun. 21, 2022.

*Primary Examiner* — Kankindi Rwego
(74) *Attorney, Agent, or Firm* — Morgan, Lewis & Bockius LLP

(57) ABSTRACT

A medical device and a method of operating the same are provided. In a method of operating a medical device for ultrasonic treatment, the medical device including an ultrasonic instrument having a vibration transmission member that vibrates ultrasonically, a power source configured to supply electric energy to the ultrasonic instrument, and a processor including a control unit operably connected to the power source, the method includes: controlling supply of the electric energy to the ultrasonic instrument, obtaining a temperature value related to a temperature of the vibration transmission member, the vibration transmission member being separate from a transducer, and controlling the power source to reduce or stop the supply of electric energy of the power source based on the rate of change of the temperature value.

20 Claims, 14 Drawing Sheets

(52) U.S. Cl.
CPC ............ *A61B 2017/320082* (2017.08); *A61B 2090/064* (2016.02)

(58) Field of Classification Search
CPC .. A61B 2017/0003; A61B 2017/00084; A61B 2017/00088; A61B 2017/00092; A61B 2017/00097; A61B 2017/00101; A61B 2017/00106; A61B 2017/0011; A61B 2017/00115; A61B 2017/00119; A61B 2017/00123; A61B 2017/00128; A61B 2017/320082; A61B 2090/064
USPC ........................................................ 606/169
See application file for complete search history.

(56) References Cited

U.S. PATENT DOCUMENTS

| | | | | |
|---|---|---|---|---|
| 2009/0036914 | A1* | 2/2009 | Houser | A61B 17/29 606/169 |
| 2011/0015660 | A1* | 1/2011 | Wiener | A61B 18/1445 606/169 |
| 2013/0282038 | A1* | 10/2013 | Dannaher | A61B 17/320068 606/1 |
| 2013/0289591 | A1* | 10/2013 | Boudreaux | A61B 18/1206 606/169 |
| 2017/0252087 | A1 | 9/2017 | Takashino et al. | |
| 2018/0333188 | A1* | 11/2018 | Nott | A61B 18/00 |
| 2019/0150974 | A1* | 5/2019 | Tsubuku | A61B 17/320092 |
| 2021/0393310 | A1 | 12/2021 | Nakamura | |

* cited by examiner

MEDICAL DEVICE AND METHOD FOR CONTROLLING THE SAME INCLUDING DISCRIMINATING END-OF-CUT CONDITIONS BASED ON TEMPERATURE

RELATED APPLICATION DATA

This application is based on and claims priority under 35 U.S.C. § 119 to U.S. Provisional Application No. 63/153,548, filed Feb. 25, 2021, the entire contents of which are incorporated herein by reference.

TECHNICAL FIELD

The systems, devices and methods disclosed herein are directed to medical devices, and in particular to medical devices for ultrasonic treatment.

BACKGROUND

In the discussion that follows, reference is made to certain structures and/or methods. However, the following references should not be construed as an admission that these structures and/or methods constitute prior art. Applicant expressly reserves the right to demonstrate that such structures and/or methods do not qualify as prior art against the present invention.

When cutting living tissue by ultrasonic vibration, the ultrasonic impedance ("US impedance") is monitored, and detection of a change of the US impedance is equated to completion of cutting of the living tissue. When such a change is detected, the ultrasonic vibration is stopped.

For example, U.S. Pat. No. 8,749,116 discloses an ultrasonic treatment apparatus which includes a treatment section to which an ultrasonic vibration is transmitted and a jaw openable and closable relative to the treatment section. In this ultrasonic treatment apparatus, when vibration generating electric power is transmitted from an electric power source to a vibration generating section, the ultrasonic vibration is generated in an ultrasonic transducer and the generated ultrasonic vibration is transmitted to the treatment section, which then treats a treated target such as a biological tissue by use of the transmitted ultrasonic vibration. Here, opening and closing directions of the jaw are perpendicular (transverse) to a transmitting direction of the ultrasonic vibration. When the ultrasonic vibration is transmitted to the treatment section in a state where the treated target is grasped between the treatment section and the jaw, frictional heat is generated between the treated target and the treatment section. By the frictional heat, the treated target is coagulated and simultaneously incised. Furthermore, in the ultrasonic treatment apparatus, an ultrasonic impedance value of the vibration generating electric power is detected with time, and it is judged whether the ultrasonic impedance value is within a range of a first default threshold or more and a second default threshold or less, with the second default threshold being greater than the first default threshold.

Also for example, U.S. Pat. No. 9,848,903 discloses calculating and detecting the ultrasonic impedance value, as well as calculating the peak of the ultrasonic impedance values at which time a cut of living tissue should be complete. However, detection of the peak of the impedance, by itself, does not always yield an accurate determination of when a cut of living tissue is complete.

Despite the above, when monitoring ultrasonic impedance, false peaks may occur before a true peak that is due to completion of cutting of the living tissue. In such situations, when the processor detects the false peak, the processor stops the ultrasonic vibration despite the procedure not being complete, e.g., the cutting of the living tissue not being complete. This can occur, for example, when treating a living tissue that has a layered structure formed of two or more layers and a false peak appears in the monitored ultrasonic impedance when the first layer is cut. Therefore, there is a need for more accurate systems and methods to detect the completion of cutting processes in treatment of living tissue with medical devices for ultrasonic treatment.

SUMMARY

The present disclosure discloses systems and methods to control a medical device for ultrasonic treatment based on the temperature behavior of the vibration transmission member, such as the rate of change in temperature at the site of a vibration transmission member of an end-effector. In some embodiments, control of a medical device for ultrasonic treatment is based on both the change of ultrasonic impedance during treatment and the temperature behavior of the vibration transmission member, such as the rate of change in temperature at the site of the vibration transmission member. Detecting both the change of ultrasonic impedance and the rate of change in temperature allows for discriminating false peaks (that are not associated with completion of cutting of living tissue being treated) from true peaks (that are associated with completion of cutting of living tissue being treated). Additionally, completion of the ultrasonic treatment, such as a cutting procedure, can by based on integrated temperature of the vibration transmission member. In further embodiments, strain values are monitored so as to detect changes in the clinician's operation of the medical device for ultrasonic treatment, such as parameters related to the back-and-forth longitudinal movement of the transmission rod, and are then correlated to the ultrasonic impedance to discriminate false peaks (that can be caused by such clinician's operation) from true peaks (that are indicative of end of treatment conditions). The present disclosure further discloses a medical device, per se, which operates based on the method for detecting the completion of the ultrasonic treatment while also incorporating methods to detect the true peak due to completion of the cut of the living tissue medical devices for ultrasonic treatment.

An object of the present disclosure is to provide a method of operating a medical device for ultrasonic treatment, the medical device including an ultrasonic instrument having a vibration transmission member that vibrates ultrasonically, a power source configured to supply electric energy to the ultrasonic instrument, and a processor including a control unit operably connected to the power source, the method including: controlling supply of the electric energy to the ultrasonic instrument, obtaining a temperature value related to a temperature of the vibration transmission member, the vibration transmission member being separate from a transducer, and controlling the power source to reduce or stop the supply of electric energy of the power source based on the rate of change of the temperature value.

Another object of the present disclosure is to provide a method of operating a medical device for ultrasonic treatment, the medical device including an ultrasonic instrument having a vibration transmission member that vibrates ultrasonically, a power source configured to provide power to an ultrasonic oscillator circuit for providing ultrasonic vibration the vibration transmission member to cut living tissue, and a processor including a control unit operably connected to the power source, the method including: calculating a plurality of temperature rate change values corresponding to a temperature increase rate per unit time, based on the temperature of the vibration transmission member, identifying a peak value among the plurality of temperature rate change values, the peak value being a largest value among the plurality of temperature rate change values, determining whether the peak value is a false peak corresponding to an incomplete cut of living tissue or a true peak corresponding to a complete cut of living tissue, when it is determined that the peak value is a false peak, then controlling the power source to reduce or stop providing power to the ultrasonic oscillator circuit, and when it is determined that the peak value is a true peak, then controlling the power source to continue providing power to the ultrasonic oscillator circuit.

Still another object of the present disclosure is to provide a medical control device, including, a power source configured to: connect to an ultrasonic instrument having a vibration transmission member that vibrates ultrasonically, and supply electric energy to the ultrasonic instrument, a processor including a control unit operably connected to the power source, the control unit being configured to: control the supply of the electric energy to the ultrasonic instrument, obtain a temperature value related to a temperature of the vibration transmission member, and control the power source to reduce or stop the supply of electric energy of the power source based on the rate of change of the temperature value.

Yet another object of the present disclosure is to provide a medical control device, including, a power source configured to provide power to an ultrasonic oscillator circuit for providing ultrasonic vibration to cut living tissue, a processor operably connected to the power source, the processor being configured to: calculate a plurality of temperature rate change values corresponding to a temperature increase rate per unit time, based on the temperature of the vibration transmission member, identify a peak value among the plurality of temperature rate change values, the peak value being a largest value among the plurality of temperature rate change values, determine whether the peak value is a false peak corresponding to an incomplete cut of living tissue or a true peak corresponding to a complete cut of living tissue, when it is determined that the peak value is a false peak, then control the power source to reduce or stop providing power to the ultrasonic oscillator circuit, and when it is determined that the peak value is a true peak, then control the power source to continue providing power to the ultrasonic oscillator circuit.

Additional features and advantages will be set forth in the description that follows, and in part will be apparent from the description, or may be learned by practice of the invention. The objectives and other advantages of the disclosed input device will be realized and attained by the structure particularly pointed out in the written description and claims thereof as well as the appended drawings.

BRIEF DESCRIPTION OF THE DRAWINGS

The disclosed aspects will hereinafter be described in conjunction with the appended drawings, provided to illustrate and not to limit the disclosed aspects, wherein like designations denote like elements.

Figure 1:
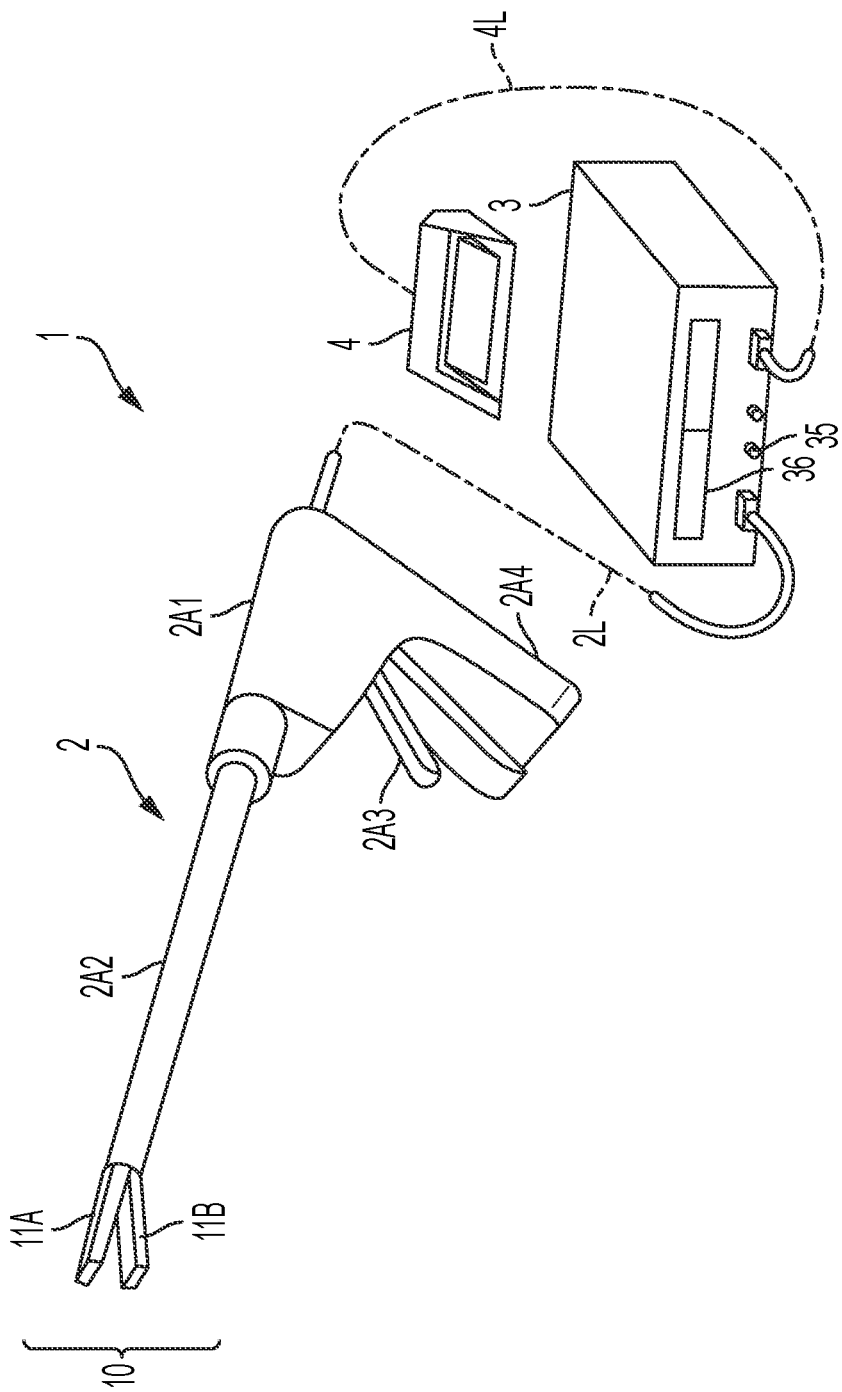
FIG. 1 shows a schematic of a medical device, in accordance with an embodiment of the present disclosure.

Throughout all of the drawings, dimensions of respective constituent elements are appropriately adjusted for clarity. For ease of viewing, in some instances only some of the named features in the figures are labeled with reference numerals.

DETAILED DESCRIPTION

Medical devices that can provide ultrasonic vibration to apply heat to a body tissue are used in various surgical procedures, for example, to cauterize the blood vessel, or to weld or seal tissues or lumens. One of the common types of devices includes an end-effector that can produce ultrasound vibration at the site of the end-effector. The end-effector includes a vibration transmission member and a pad that are moved to come into contact with each other. When living tissue is cut by ultrasonic vibration in the vibration transmission member, a processor monitors ultrasonic impedance. The processor detects completion of cut of the living tissue based on the change of the ultrasonic impedance, and stops (or reduces) the ultrasonic vibration.

After the ultrasonic treatment is started, the living tissue is denatured by frictional heat and hardened, and the ultrasonic impedance increases. The living tissue is cut, and the vibration transmission member and pad come into contact with each other. The ultrasonic impedance decreases as the pad is denatured due to frictional heat generated by ultrasonic vibration. By detecting a point (peak) at which the ultrasonic impedance changes from an increase to a decrease, it is possible to detect the completion of cut of the living tissue. The wear of the pad can be suppressed by speeding up the detection of completion of cut of the living tissue. It is thus possible to suppress excessive invasion of the living tissue.

However, depending on type of the living tissue, another peak, i.e., a "false peak," may occur before the peak, i.e., the "true peak," due to completion of the cut of the living tissue. When the processor detects the false peak, the processor reduces or stops the ultrasonic vibration despite there being no completion of the cut of the living tissue. When the living tissue is a layered structure formed of two or more layers, e.g., a cervix, it is possible that the false peak may appear when the first layer is cut. Embodiments detect the completion of cut of the living tissue by detecting the peak in the change of ultrasonic impedance and by monitoring the change of the rate of increase of the temperature of the vibration transmission member. Some embodiments detect the completion of cut of the living tissue by monitoring the change of the rate of increase of the temperature of the vibration transmission member without detecting the impedance.

Accordingly, one aspect of the present disclosure describes a method for accurately detecting the true peak due to completion of the cut of the living tissue. The present disclosure further describes control of the medical device based on the rate of change in temperature at the site of the vibration transmission member of the end-effector or based on both the change of ultrasonic impedance during treatment and the rate of change in temperature, such as the rate of change in temperature at the site of the end-effector. Detecting both the change of ultrasonic impedance and the rate of change in temperature allows for discriminating false peaks (that are not associated with completion of cutting of living tissue being treated) from true peaks (that are associated with completion of cutting of living tissue being treated). In another aspect, the present disclosure further relates to a medical device for ultrasonic treatment, per se, which operates based on the method for detecting the true peak due to completion of the cut of the living tissue.

The term "patient," as used herein, comprises any and all organisms and includes the term "subject." A patient can be a human or an animal.

As used herein, the temperature of the vibration transmission member specifically indicates the temperature of the tip. In the following description and examples, the temperature of the vibration transmission member is treated in the same manner. The temperature is, for example, calculated based on the current and voltage supplied to the vibration transmission member, or acquired by various known methods.

FIG. 1 shows a schematic of a medical device, in accordance with an embodiment of the present disclosure. As shown in FIG. 1, the medical device 1 for treating a tissue of a patient is provided with a treatment instrument 2, a controller 3 having a processor includes an input controller 4, such as an actuation switch. The treatment instrument 2 may be, for example, a surgical operation energy inosculation apparatus used for welding biological tissue, such as in an abdominal cavity through an abdominal wall, or incising, such as in an open surgery procedure or laparoscopy.

The treatment instrument 2 has a grip 2A1, a shaft 2A2, and a treatment section constituted by an end-effector 10 such as, for example, an openable or pivoting pair of grasping sections (including a first grasping section 11A and a second grasping section 11B) for grasping biological tissue to perform treatment. The grasping sections as whole are also referred to herein as the "treatment portion" or the "treatment section" of the medical instrument. Note that, hereinafter, at time of mentioning each of components having a same function and having reference numerals with A and B attached to ends of the reference numerals, respectively, the symbol A or B may be omitted. For example, each of the first grasping section 11A and the second grasping section 11B may be referred to as the grasping section.

The grip 2A1 is connected to the controller 3 via a cable 2L. The grip 2A1 has an opening/closing actuator 2A3, such as a trigger, for a surgeon to operate opening and closing of the treatment section and is in such a shape that the surgeon can easily clasp, for example, in a substantially L shape. The opening/closing actuator 2A3 is arranged at one end of the grip 2A1 and is integrated with the treatment section to transmit operation of the opening/closing actuator 2A3 to the treatment section. On the other side of the grip 2A1, a grasping portion 2A4 is provided for a clinician to grasp when operating the instrument 2.

Figure 2:
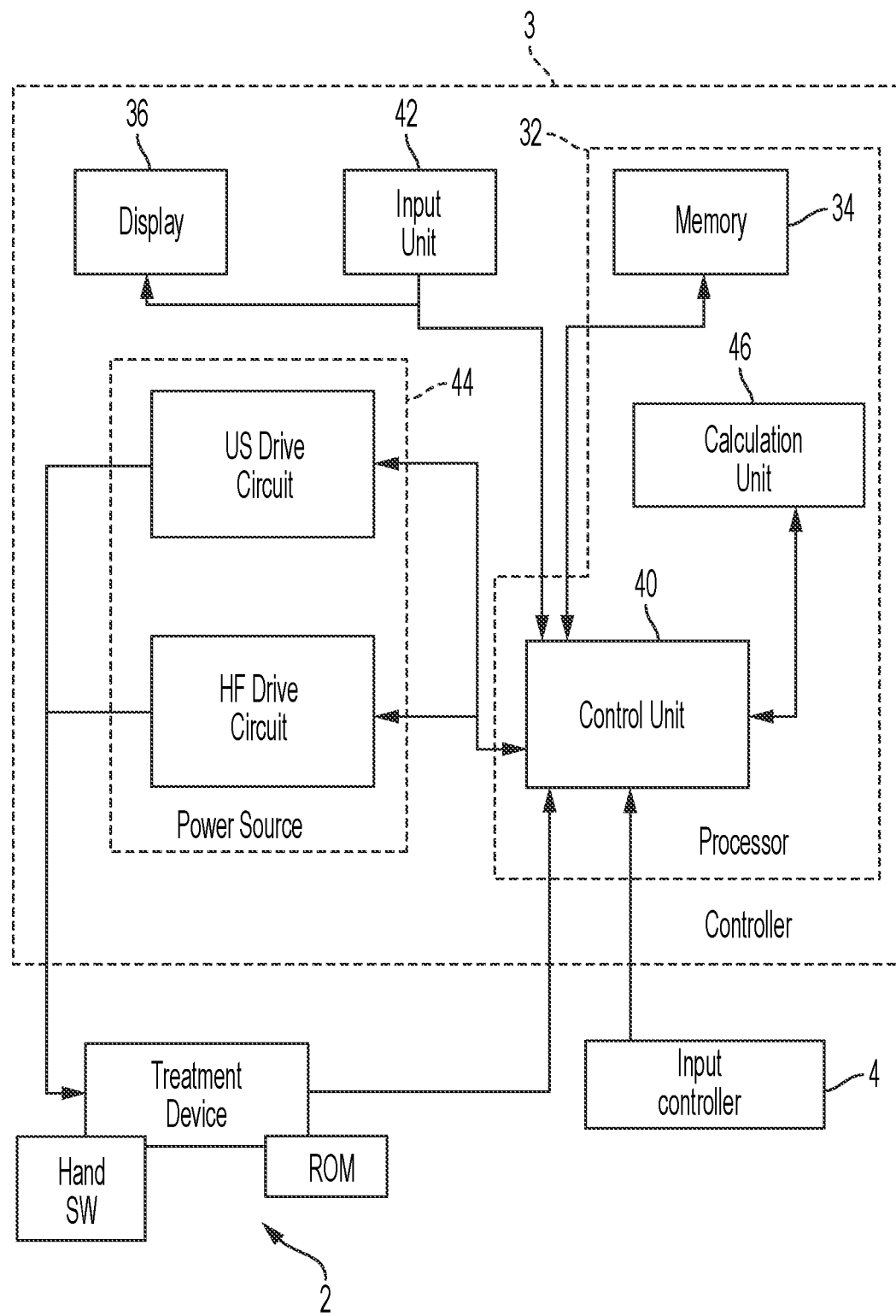
FIG. 2 shows a schematic of a controller in accordance with an embodiment of the present disclosure.

FIG. 2 shows a schematic of a controller in accordance with an embodiment of the present disclosure. The controller 3 may include a processor 32, a display 36, an input unit 42, and a power source 44.

The processor 32 may include a memory 34, a calculation unit 46 and a control unit 40. The calculation unit 46 and the control unit 40 are formed of an integrated circuit including a CPU (Central Processing Unit), an ASIC (Application Specific Integrated Circuit) or an FPGA (Field Programmable Gate Array). The calculation unit 46 and the control unit 40 may be formed as a single integrated circuit, or may be formed of a plurality of integrated circuits.

In some embodiments, various parameters used for estimating a current temperature such as, for example, the specific heat capacity of the treatment portion, the thermal resistance of the treatment portion, the thermal conductivity of the treatment portion, or a contact area between the body tissue and the treatment portion, any of which may be stored in memory 34, e.g., in a look-up table stored in the memory 34. The look-up table may include the values of the corresponding parameters for different treatment portions. For example, the look-up table may include the parameters for muscle tissue, adipose tissue, blood vessels, intestinal wall, or other tissue types. In such embodiments, estimating the current temperature may include determining the type of tissue on which the procedure is being performed, and determining the corresponding parameter values in the look-up table for estimating the current temperature. Alternatively, the procedure name may be used as the basis for entry into the look-up table. The calculation unit 46 is configured to compute the estimated current temperature as well as other parameters that are needed for computing the estimated current temperature and rate of change of temperature, which may require estimating a current temperature. In such embodiments, for example, estimating the current temperature may include determining the type of biological tissue on which the procedure is being performed, and determining the corresponding parameter values in the look-up table for estimating the current temperature. Alternatively, the procedure name may be used as the basis for entry into the look-up table. The control unit 40 is configured to control the power source 44 and the display 36 based on the commands provided by the processor 32 using the parameters computed by the calculation unit 46. A temperature may be determined, sensed, or calculated, by suitable devices and methods, for example, as disclosed in U.S. Provisional Patent Application Ser. No. 63/042,594, filed on Jun. 23, 2020, titled "A METHOD FOR CONTROLLING A MEDICAL DEVICE AND A MEDICAL DEVICE IMPLEMENTING THE SAME", the entire contents of which are incorporated herein by reference.

In some embodiments, the data related to the various parameters is a value of the contact area calculated using size and shape of the end-effector, in particular, the treatment portion of the end-effector, and how the end-effector is used (e.g., related to the procedure) and this data is stored in the memory in advance. In addition, as the contact area changes as the end-effector grasps and regrasps tissue during the medical procedure, the various parameters can also correspondingly change during the medical procedure, and having the data for the various parameters readily available in memory allows for dynamic updating during the medical procedure.

The display section 36, which displays treatment conditions and the like, and a setting operation section 35 for the surgeon to set the treatment conditions and the like on a front panel. In some embodiments, a input controller 4 may be connected to the controller 3 via a cable 4L. The clinician may turn the power output from the controller 3 to the treatment instrument 2 ON or OFF by an input controller 4, such as by pressing a pedal of a foot switch of the input controller 4. The foot switch is not an essential component and any input controller can be utilized, such as a switch or the like which the clinician operates by hand or other alternative input controller.

In some embodiments, the controller 3 includes a processor 32, which controls the application of power to the instrument 2 via the power source 44 so as to maintain a temperature at the end-effector 10 in a safe and effective range. In some embodiments, the processor 32 may override the input provided by the clinician (e.g., through the input controller 4) for turning the power to the instrument 2 ON or OFF.

In some embodiments, the control unit 40 may be configured to cause the instrument 2 to increase or decrease a grasping force with which the instrument 2 or the end-effector 10 thereof grasps the portion of tissue on which the procedure is being performed.

Figure 3:
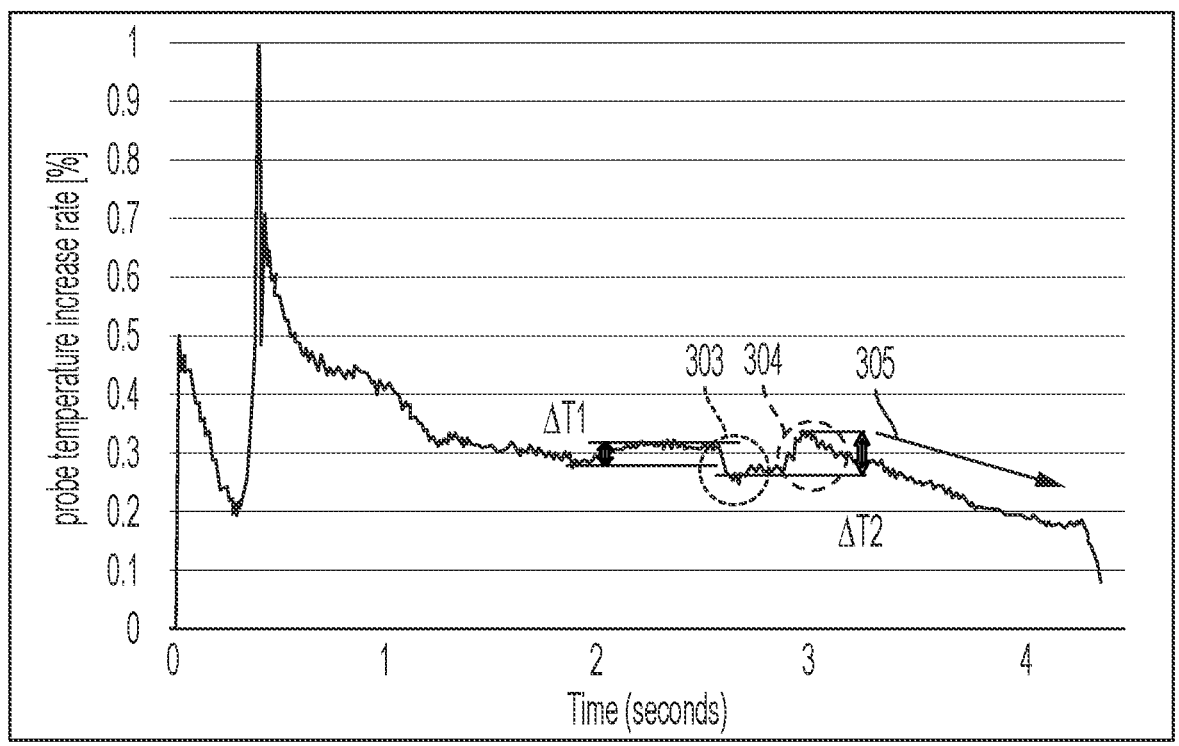
FIG. 3 is a graph showing a rate of increase of temperature (in %) over time (in seconds) in a medical device, in accordance with an embodiment of the present disclosure.

FIG. 3 is a graph showing a rate of increase of temperature (in %) over time (in seconds) in a medical device, in accordance with an embodiment of the present disclosure. FIG. 3 shows that the completion of the cut of the living tissue can be detected by the rate of change of the increase of the temperature ($\Delta T$, in %) of the vibration transmission member during treatment according to some embodiments. An incomplete cut 303 (dashed circle) has the first rate of change of temperature ($\Delta T1$), which is less than the threshold ($\Delta T_{th}$). The peak of the rate of change of the increase of temperature at the incomplete cut 303 is a false peak where there is a temporary drop in the rate of change of the increase of temperature before it increases again. A complete cut 304 (solid circle) has the second rate of change of temperature ($\Delta T2$), which is greater than the threshold ($\Delta T_{th}$). The peak of the rate of change of the increase of temperature at the complete cut 304 is a true peak. The rate of change of the increase of the temperature will then drop after the cut is complete (arrow 305).

Figure 4:
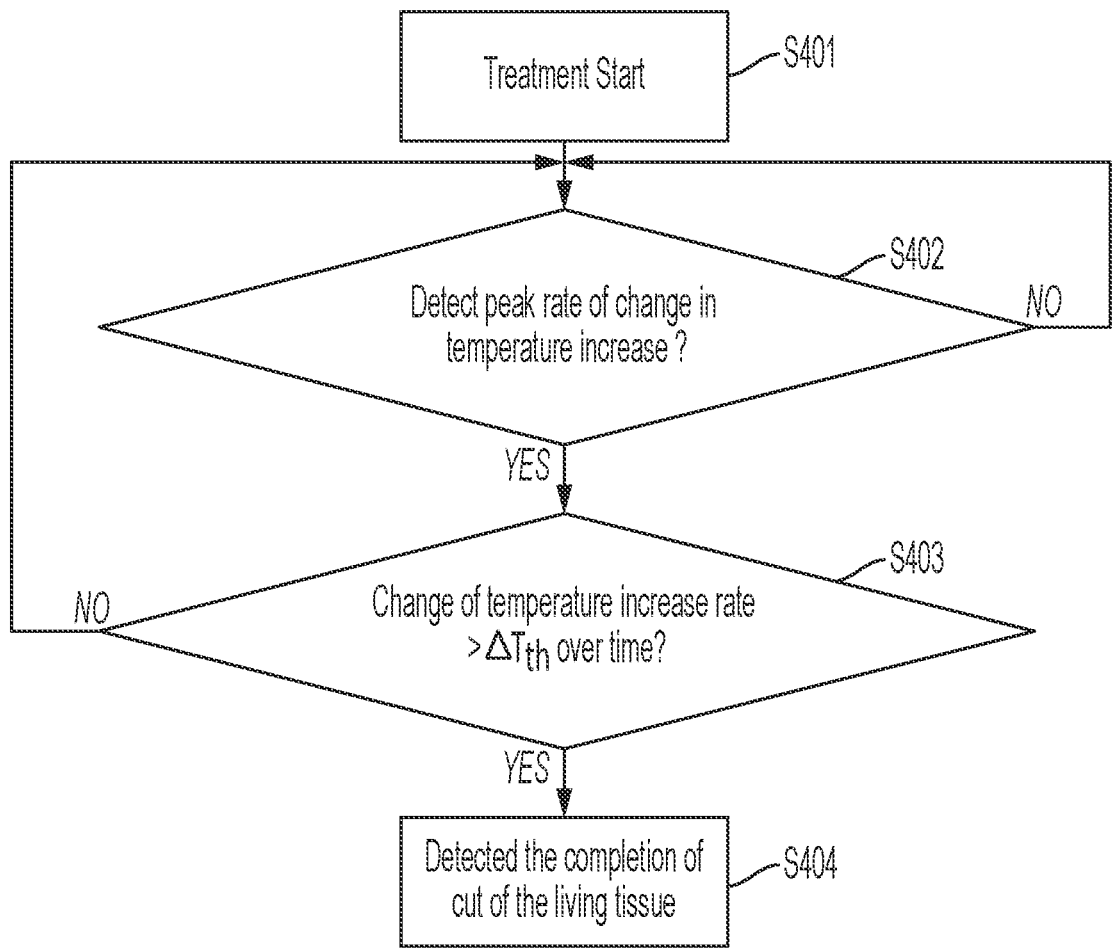
FIG. 4 is a flow chart for a process of detecting completion of a cut of living tissue, in accordance with an embodiment of the present disclosure.

FIG. 4 is a flow chart for a process of detecting completion of a cut of living tissue, in accordance with an embodiment of the present disclosure. In operation S401, the ultrasonic treatment is started. In operation S402, a determination is made whether a peak has been detected in the rate of change of the increase of the temperature of the vibration transmission member during treatment. If "NO", then treatment continues with operation S402. If "YES", then a determination is made whether the change of temperature increase rate is greater than the threshold value ($\Delta T_{th}$) over a certain period of time (S403). If "NO", then treatment continues with operation S402. If "YES", then it is determined that the cut of the living tissue has been completed, and treatment stops (or is reduced) (S404).

Figure 5:
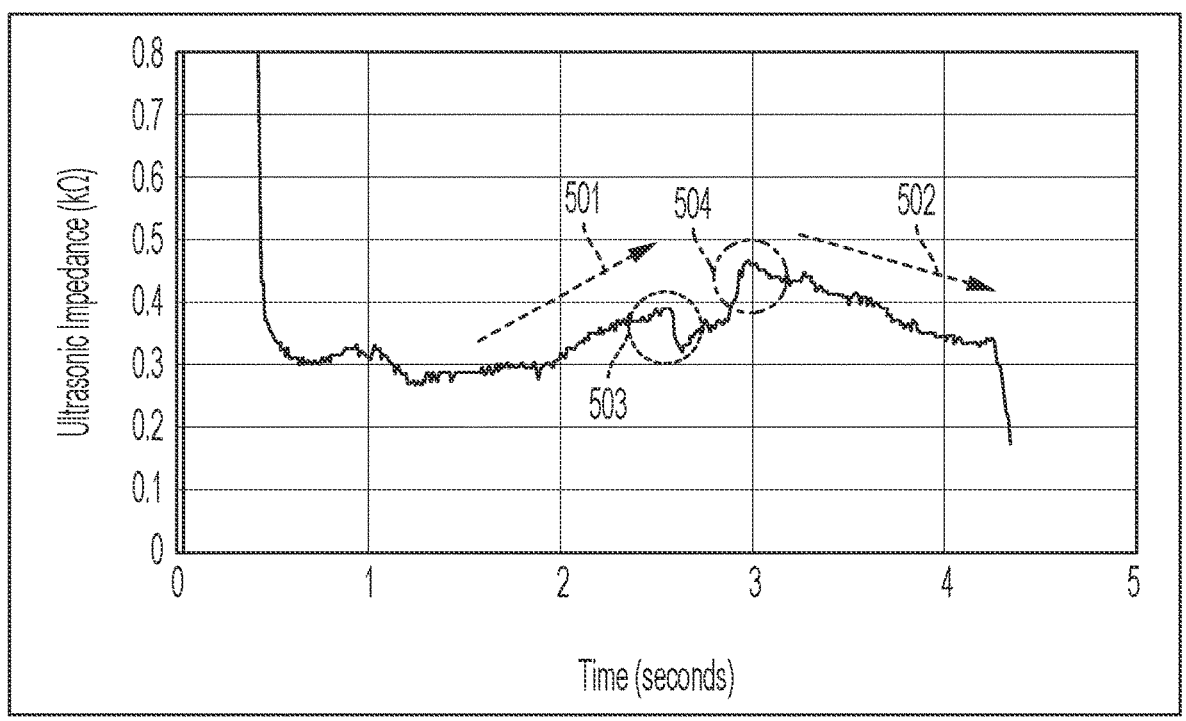
FIG. 5 is a graph showing ultrasonic impedance (in kiloohms (kΩ)) over time (in seconds) in a medical device, in accordance with an embodiment of the present disclosure.

FIG. 5 is a graph showing ultrasonic impedance (in kiloohms (k$\Omega$)) over time (in seconds) in a medical device, in accordance with an embodiment of the present disclosure. With reference to FIG. 5, ultrasonic impedance of the ultrasonic transmission member may be concurrently monitored in accordance with an embodiment of the present disclosure. FIG. 5 shows that, while the ultrasonic impedance is being monitored, the impedance will generally increase (arrow 501) until the cut is completed, then will decrease (arrow 502) until power is stopped or reduced. However, a false impedance peak 503 may be detected (dashed circle) where there is a temporary drop in impedance, followed by another increase in impedance until the true impedance peak 504 (solid circle).

Figure 6A:
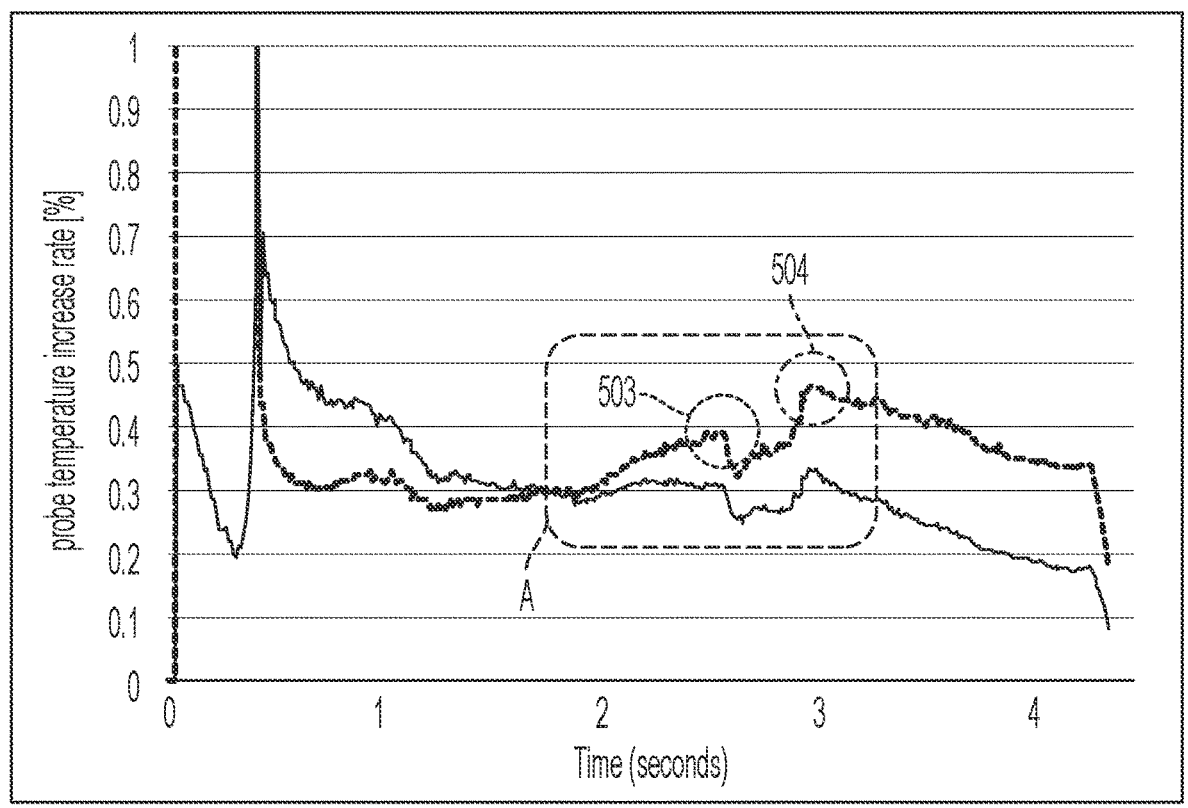
FIG. 6A is a graph showing a rate of increase of temperature (in %) over time (in seconds), along with the ultrasonic impedance (in kiloohms (kΩ)) over time (in seconds) as in FIG. 5, in a medical device, in accordance with an embodiment of the present disclosure.
Figure 6B:
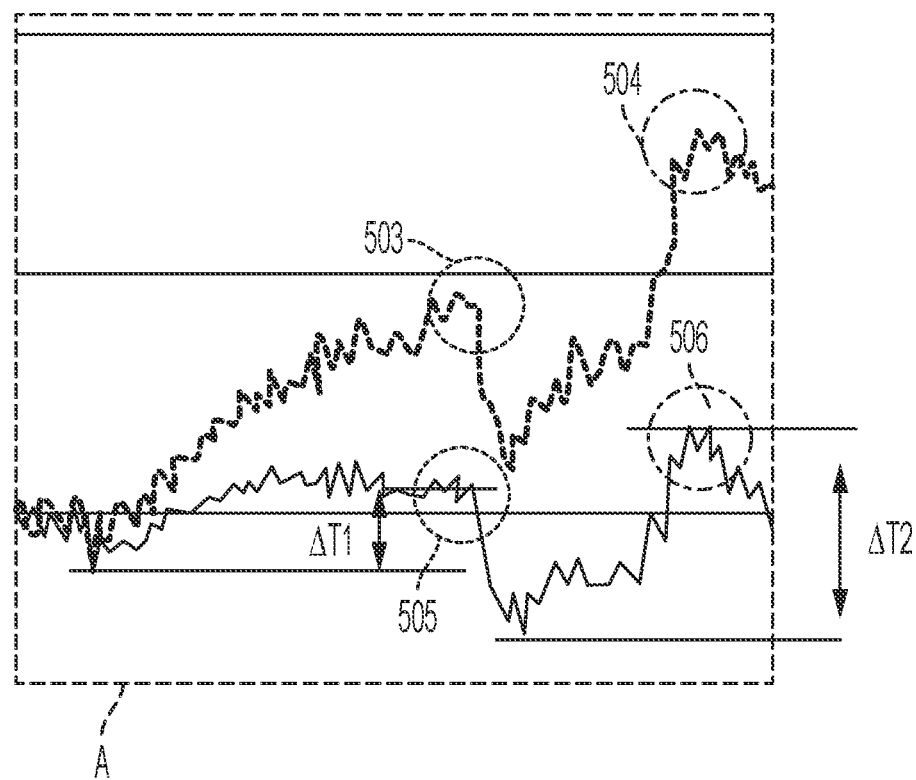
FIG. 6B is a detail of portion A of the graph of FIG. 6A.

FIG. 6A is a graph showing a rate of increase of temperature (in %) over time (in seconds) from FIG. 3 overlaid based on time with the ultrasonic impedance (in kiloohms (k$\Omega$)) over time (in seconds) from FIG. 5 in a medical device, in accordance with an embodiment of the present disclosure. FIG. 6B is a detail of a portion A of the graph of FIG. 6A. In embodiments, the temperature increase rate per unit time is calculated based on the temperature of the vibration transmission member. To determine that the first peak is a false impedance peak 503, the rate of change in the temperature ($\Delta T$) at the corresponding time period is analyzed. For example, the rate of change in the temperature ($\Delta T$) is calculated, as discussed above, and is compared to a threshold value ($\Delta T_{th}$). In the temperature behavior corresponding to the peak of ultrasonic impedance, if the increase ($\Delta T$) from the minimum of the temperature increase rate of the vibration transmission member is smaller than a threshold value ($\Delta T_{th}$), then that peak of ultrasonic impedance is determined to be a false peak. However, in the temperature behavior corresponding to the peak of ultrasonic impedance, if the increase ($\Delta T$) from the minimum of the temperature increase rate of the vibration transmission member is larger than the threshold value ($\Delta T_{th}$), then that peak of ultrasonic impedance is determined to be a true peak. With reference to FIGS. 6A-6B, the difference in the first rate of change of temperature ($\Delta T1$) at the false impedance peak 503, taken at the time associated with the temperature at 505, is less than a threshold value ($\Delta T_{th}$), while the difference in the second rate of change of temperature ($\Delta T2$) at the true peak 504, taken at the time associated with the temperature at 506, is greater than the threshold value ($\Delta T_{th}$).

Figure 6C:
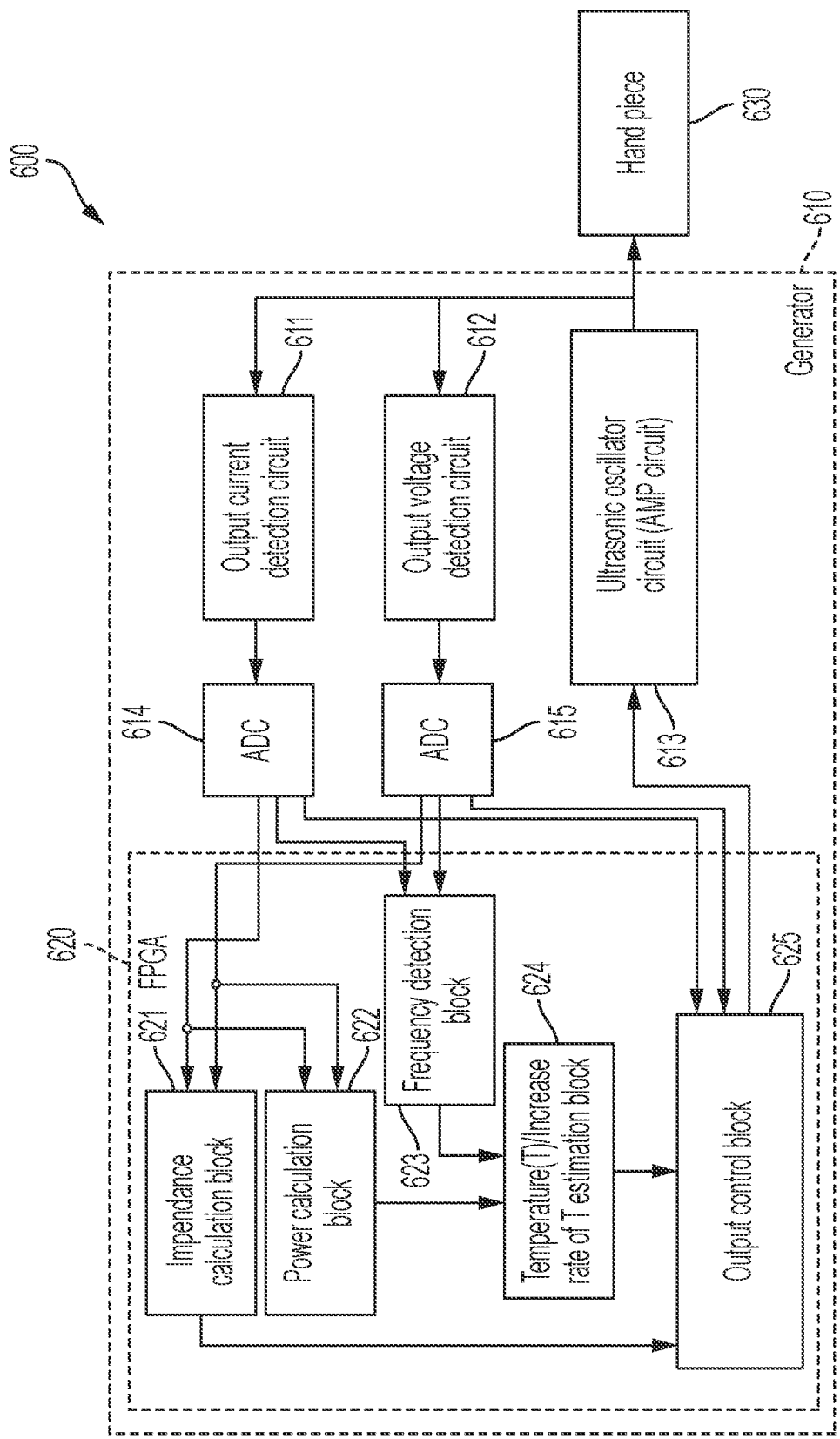
FIG. 6C is a block diagram of a functional operation of the medical device in accordance with the embodiment of FIG. 6A.

FIG. 6C is a block diagram of a functional operation of the medical device in accordance with the embodiment of FIG. 6A.

The functional blocks of FIG. 6C may be operated, for example, by the processor 32 of FIG. 2. In an embodiment 600, a generator 610 may be controlled by a field-programmable gate array (FPGA) 620, programmable circuit, or other integrated circuit, and may control a hand piece 630, e.g., the treatment instrument 2 of FIG. 1.

The generator 610 may include an ultrasonic oscillator circuit 613, e.g., an amplifier circuit, an output current detection circuit 611, an output voltage detection circuit 612, and analog-to-digital converters (ADCs) 614, 615. The ultrasonic oscillator circuit 613 outputs an ultrasonic oscillation signal to the hand piece 630. The output current detection circuit 611 detects the current of the ultrasonic oscillation signal from the ultrasonic oscillator circuit 613. The output voltage detection circuit 612 detects the voltage of the ultrasonic oscillation signal from the ultrasonic oscillator circuit 613. The output current detection circuit 611 and the output voltage detection circuit 612 output analog signals, corresponding to their respective detected values, to respective analog-to-digital converters 614, 615.

The FPGA 620 may include an impedance calculation block 621 for calculating impedance, a power calculation block 622 for calculating how much power has been supplied, a frequency detection block 623 for detecting a vibration frequency of the medical device, a temperature (t)/increase rate of T estimation block 624 for calculating the increase ($\Delta T$) from the minimum of the temperature increase rate of the vibration transmission member, and an output control block 625 for controlling output of the ultrasonic oscillator circuit 613 of the generator 610. Each of the ADCs 614, 615 of the generator 610 outputs to the impedance calculation block 621, the power calculation block 622, the frequency detection block 623, and the output control block 625. The power calculation block 622 and the frequency detection block 623 output to the temperature (t)/increase rate of T estimation block 624. A minimum value and a peak value of the temperature increase rate is detected at the temperature (t)/increase rate of T estimation block 624. The output control block 625 receives results from the temperature (t)/increase rate of T estimation block 624 and the impedance calculation block 621, and uses those results along with the values from the ADCs 614, 615 to control the ultrasonic oscillator circuit 613. As discussed above, if the temperature (t)/increase rate of T estimation block 624 determines that the increase ($\Delta T$) from the minimum of the temperature increase rate of the vibration transmission member is smaller than a threshold value, it is determined to be a false peak, and the output control block 625 controls the ultrasonic oscillator circuit 613 to continue to operate. If the temperature (t)/increase rate of T estimation block 624 determines that the increase ($\Delta T$) from the minimum of the temperature increase rate of the vibration transmission member is larger than the threshold value, it is determined to be a true peak, and the output control block 625 controls the ultrasonic oscillator circuit 613 to reduce or stop operation and cease transmission of oscillation to the hand piece 630.

Figure 7:
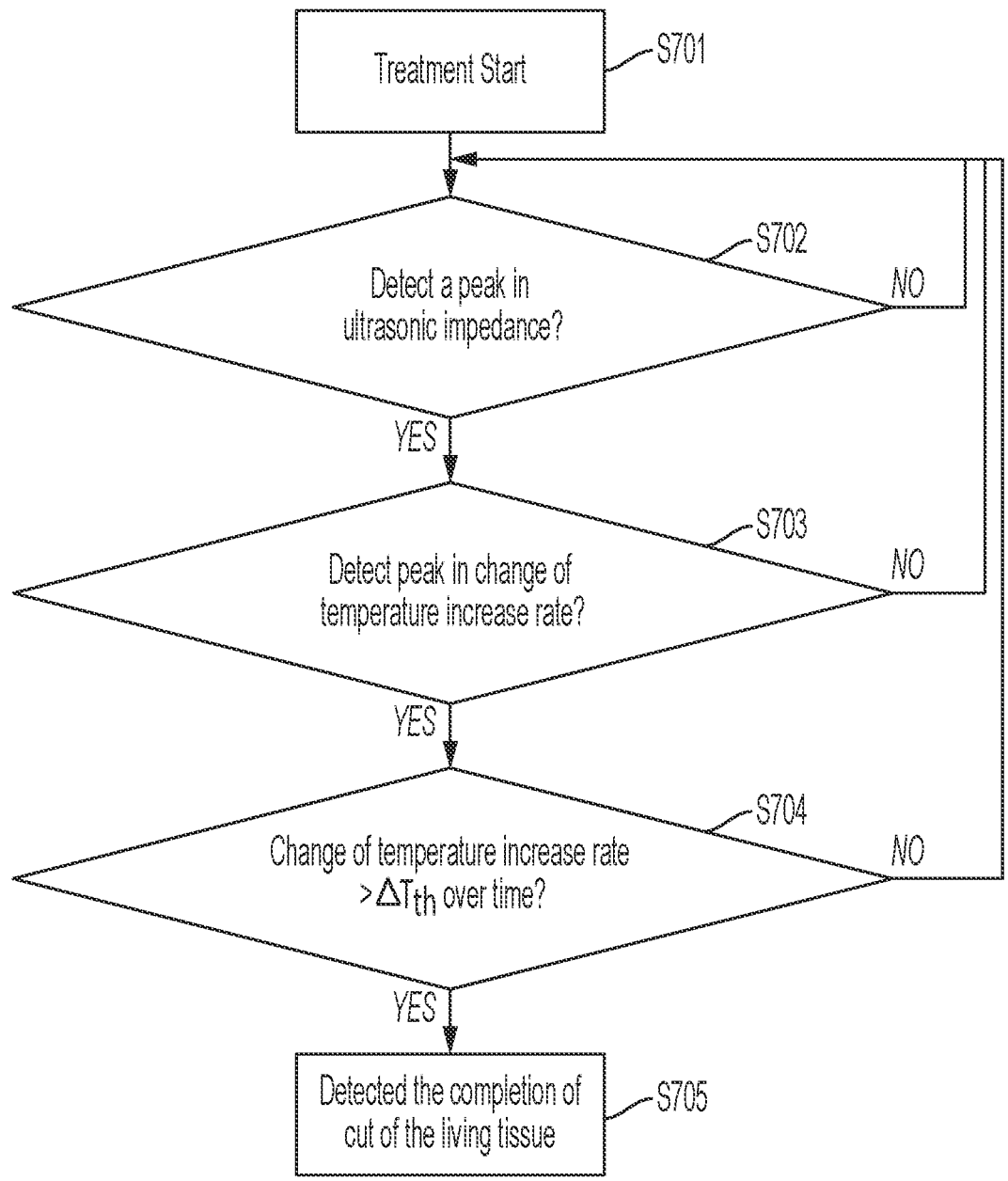
FIG. 7 is a flow chart for a process of detecting completion of a cut of living tissue, in accordance with another embodiment of the present disclosure.

FIG. 7 is a flow chart for a process of detecting completion of a cut of living tissue, in accordance with an embodiment of the present disclosure. In operation S701, the ultrasonic treatment is started. In operation S702, a determination is made whether a peak has been detected in the ultrasonic impedance of the vibration transmission member during treatment based on the power supplied to the vibration transmission member. If "NO", then treatment continues with operation S702. If "YES", then, in operation S703, a determination is made whether a peak has been detected in the rate of change of the increase of the temperature of the vibration transmission member during treatment. If "NO", then treatment continues with operation S702. If "YES", then a determination is made whether the change of temperature increase rate is greater than the threshold value $T_{th}$ over a certain period of time (S704). If "NO", then treatment continues with operation S702. If "YES", then it is determined that the cut of the living tissue has been completed, and treatment stops (or is reduced) (S705). It should be appreciated that operation S702 may be performed after or concurrently with operations S703 and S704.

Figure 8:
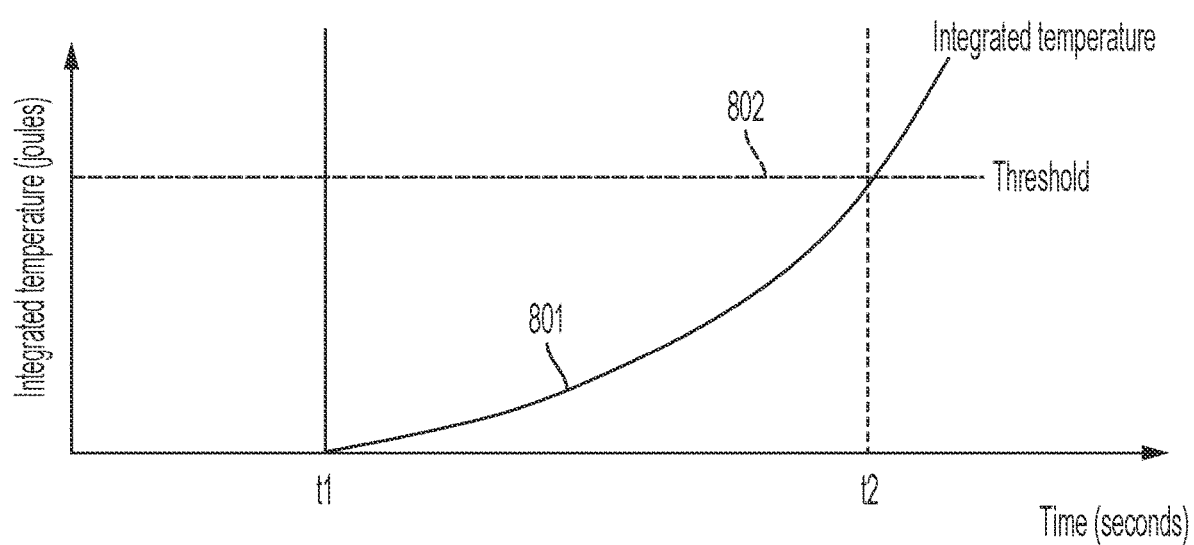
FIG. 8 is a graph showing integrated temperature (in Joules) over time (in seconds) in a medical device, in accordance with an embodiment of the present disclosure.

FIG. 8 is a graph showing integrated temperature over time in a medical device, in accordance with an embodiment of the present disclosure. With reference to FIG. 8, some embodiments may detect whether the living tissue is cut only by the integrated temperature of the vibration transmission member. In other embodiments, the integrated temperature may also be used in addition to the above-discussed rate of change of the temperature increase and/or impedance. The integrated temperature can be determined by calculating the amount of energy, e.g., in joules (J), at the tip of the medical device, e.g., at the distal tip of the vibration transmission member of the end-effector 10 of FIG. 1. The calculation may be performed by integrating the temperature of the vibration transmission member. The memory 34 may include information about protein denaturation temperatures of various tissues to determine whether the tissue has been cut. At time t1, line 801 starts integrating the temperature of the vibration transmission member while ultrasonic energy is being supplied. At time t2, when the calculated integrated temperature reaches a threshold at line 802, output is stopped (or reduced) and treatment ends.

Figure 9:
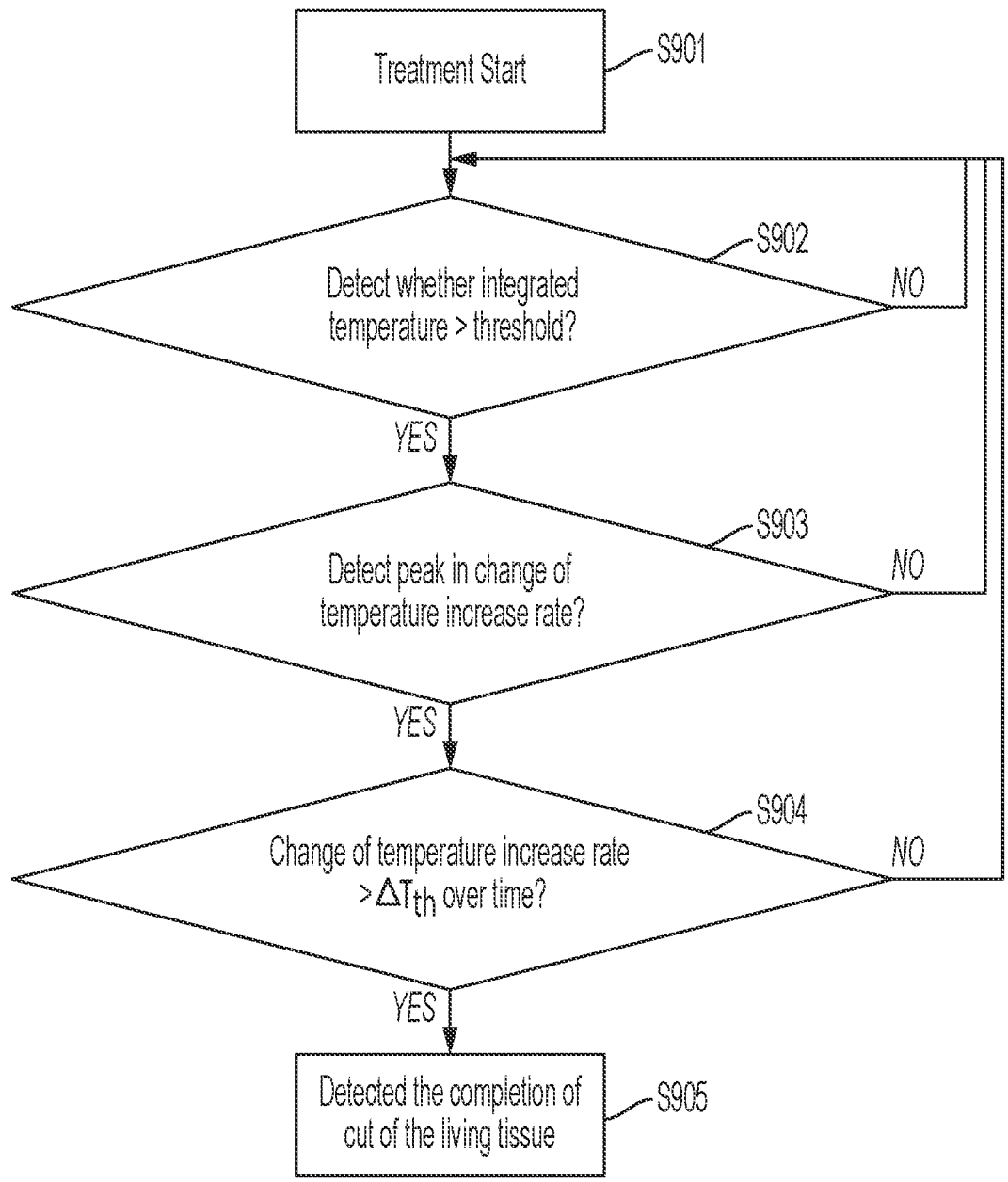
FIG. 9 is a flow chart for a process of detecting completion of a cut of living tissue, in accordance with a further embodiment of the present disclosure.

FIG. 9 is a flow chart for a process of detecting completion of a cut of living tissue, in accordance with an embodiment of the present disclosure. In operation S901, the ultrasonic treatment is started. In operation S902, a determination is made whether a peak has been detected in the ultrasonic impedance of the vibration transmission member during treatment. If "NO", then treatment continues with operation S902. If "YES", then, in operation S903, a determination is made whether a peak has been detected in the rate of change of the increase of the temperature of the vibration transmission member during treatment. If "NO", then treatment continues with operation S902. If "YES", then a determination is made whether the change of temperature increase rate is greater than the threshold value $T_{th}$ over a certain period of time (S904). If "NO", then treatment continues with operation S902. If "YES", then it is determined that the cut of the living tissue has been completed, and treatment stops (or is reduced) (S905). It should be appreciated that operation S902 may be performed after or concurrently with operations S903 and S904.

Figure 10A:
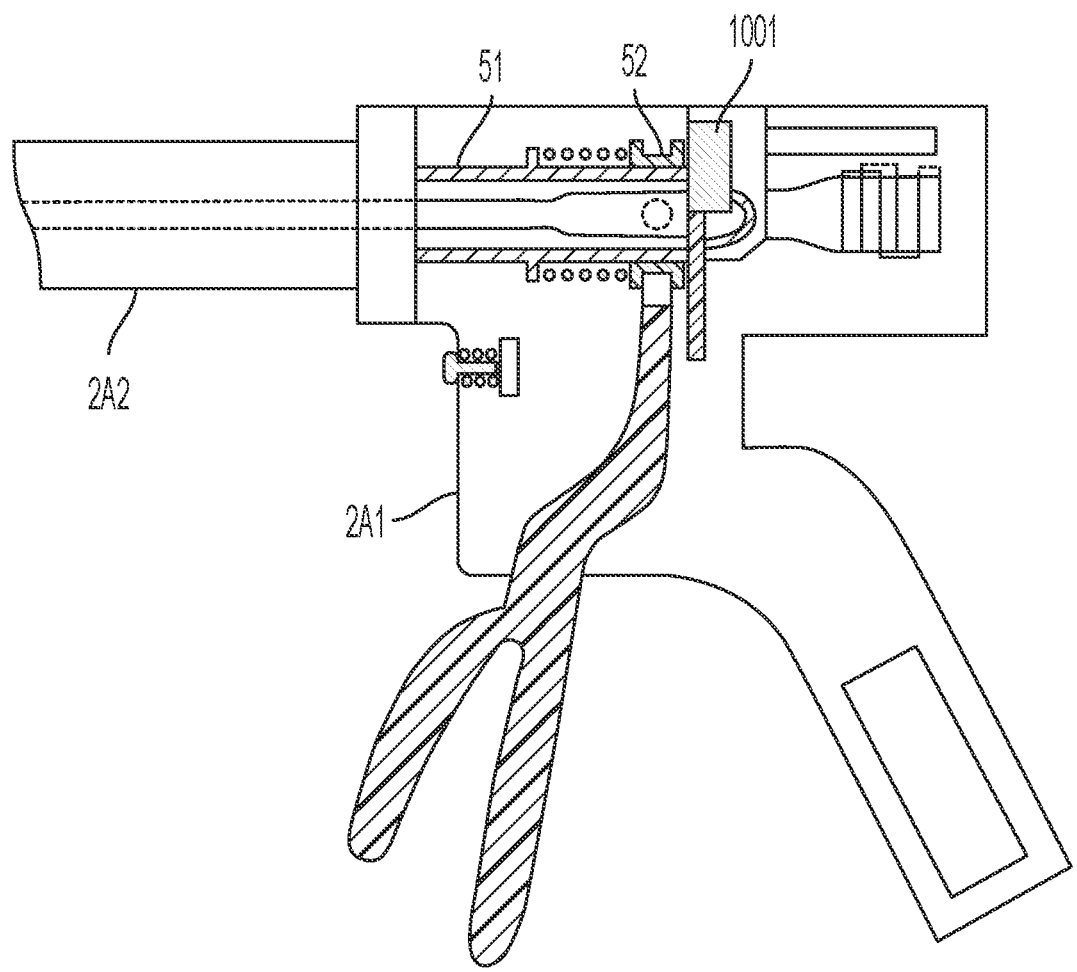
FIG. 10A is a cross-section of a medical device, in accordance with an embodiment of the present disclosure.
Figure 10B:
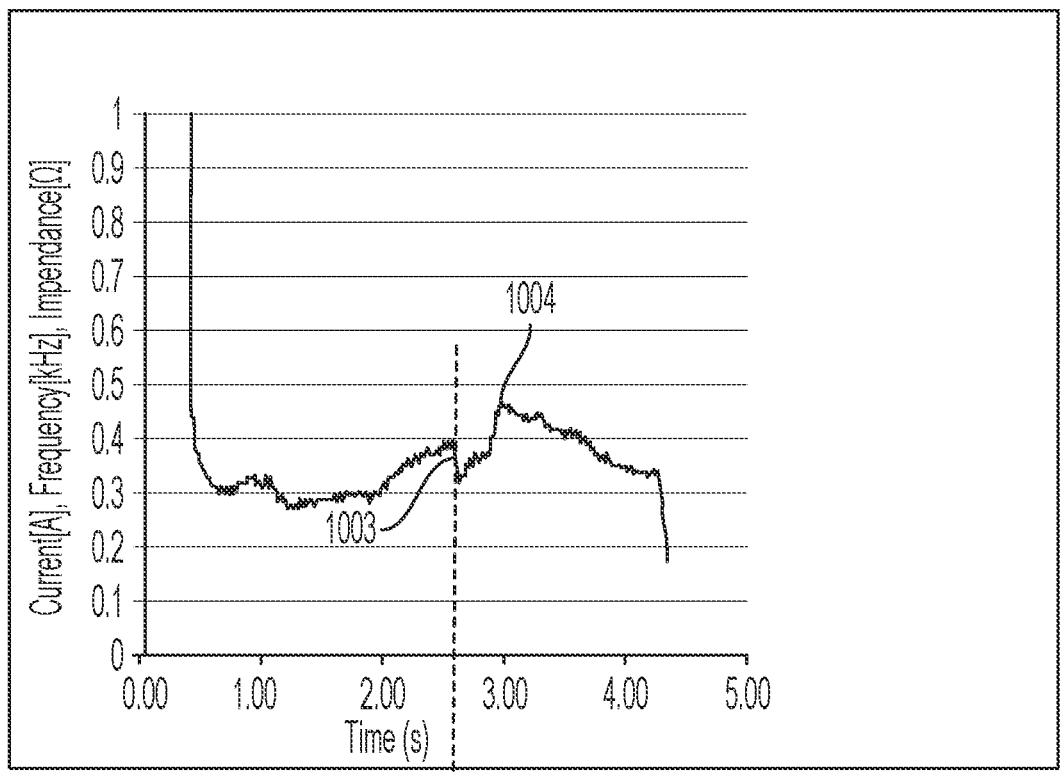
FIG. 10B is a graph showing operation of the medical device of FIG. 10A in which a peak feature in the ultrasonic impedance (in kiloohms (kΩ)) over time (in seconds) in a medical device (graph at (I)) is correlated to a peak feature in the strain (in microstrain (με) over time (in seconds) in the medical device (graph at (II)).
Figure 10B:
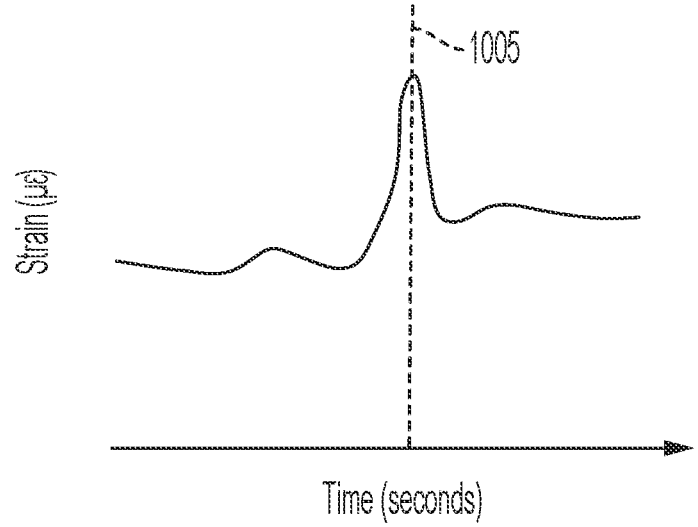

FIG. 10A is a cross-section of a medical device, in accordance with an embodiment of the present disclosure. FIG. 10B is a graph showing operation of the medical device of FIG. 10A. With reference to FIGS. 1 and 10A-10B, the shaft 2A2 of the medical device 1 of FIG. 1 may extend internally to the grip 2A1. The internal portion of the shaft 2A2 may include an internal shaft 51 and a slider 52 that contributes to the longitudinal movement of the internal shaft 51. A force sensor 1001, e.g., a strain sensor, may be installed at the end of the slider 52 for detecting the gripping force of the clinician operating the medical device. A change in the gripping force means that the back-and-forth movement of the shaft is being generated. The force sensor 1001 (e.g., strain sensor) is used to detect a strain, which is a stress in the long axis direction generated by the longitudinal movement of the shaft, after the output is started. In other words, a higher strain detected by the force sensor 1001 means that the clinician is squeezing the opening/closing actuator 2A3 harder. In combination with detecting the change in the rate of increase of temperature, as in the FIG. 7 example, if the change in the amount of the strain, i.e., a distortion value, exceeds a certain range or exceeds a certain rate of change, it is determined to be a false peak. For example, the clinician may want to continue cutting, and so is gripping harder. In FIG. 10B, part (I) shows the change in the rate of increase of temperature, similarly to the FIG. 7 example, with the false peak 1003 and true peak 1004. Part (II) shows the strain value detected by the force sensor 1001 of FIG. 10A. If the amount of strain at the corresponding time, e.g., as indicated by line 1005, exceeds a threshold, then the peak 1003 is occurring at the same time as the distortion value in strain is occurring, such that a false peak is determined.

Figure 11:
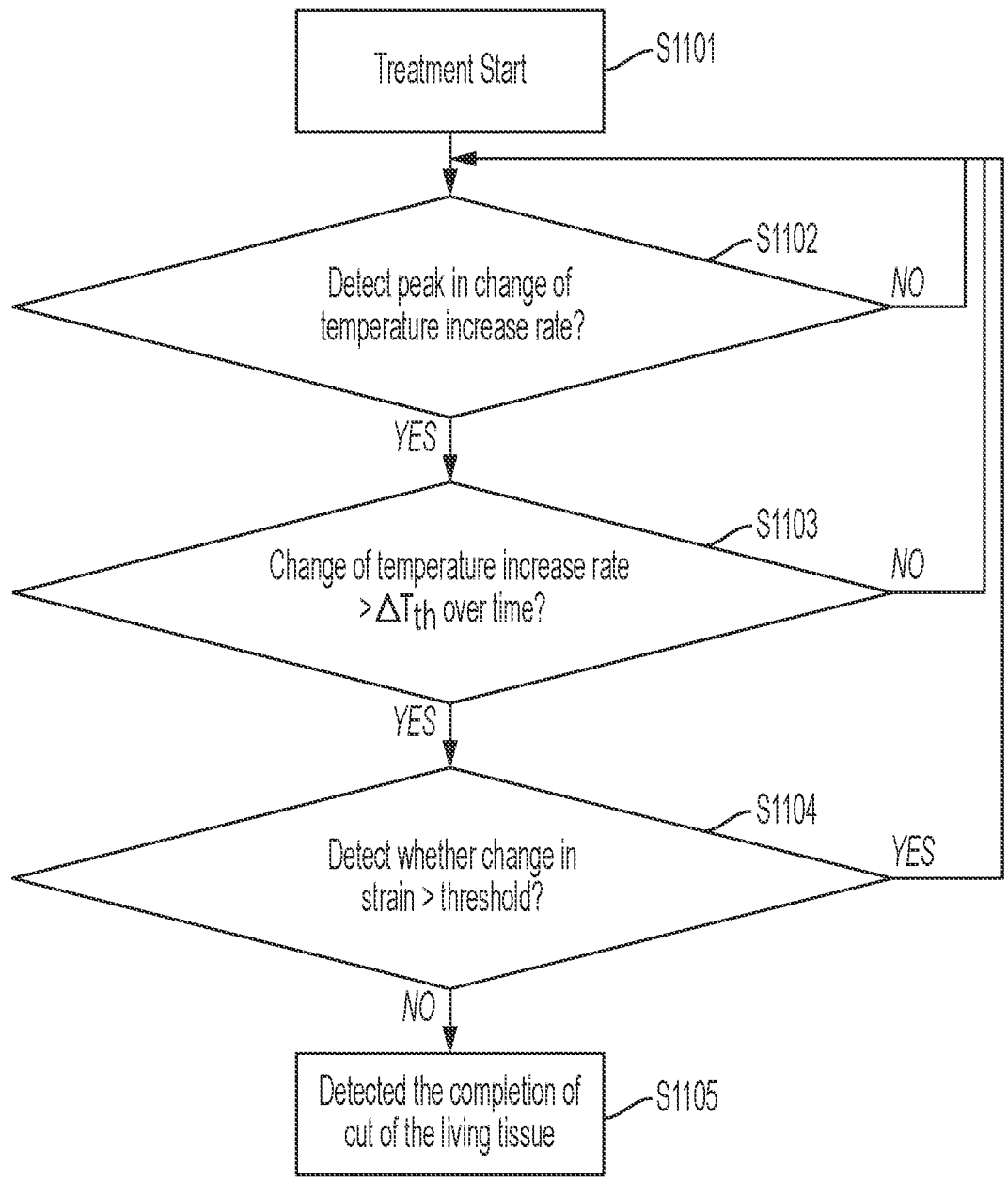
FIG. 11 is a flow chart for a process of detecting completion of a cut of living tissue, in accordance with a still further embodiment of the present disclosure.

FIG. 11 is a flow chart for a process of detecting completion of a cut of living tissue, in accordance with an embodiment of the present disclosure. In operation 51101, the ultrasonic treatment is started. In operation S1102, a determination is made whether a peak has been detected in the rate of change of the increase of the temperature of the vibration transmission member during treatment. If "NO", then treatment continues with operation S1102. If "YES", then a determination is made whether the change of temperature increase rate is greater than the threshold value $T_{th}$ over a certain period of time (S1103). If "NO", then treatment continues with operation S1102. If "YES", then, in operation S1104, a determination is made whether a change in the strain value detected by the force sensor 1001 of FIG. 10A is greater than a threshold. If "YES", then treatment continues with operation S1102. If "NO", then, it is determined that the cut of the living tissue has been completed, and treatment stops (or is reduced) (S1105). It should be appreciated that operation S1104 may be performed before or concurrently with operations S1102 and S1103.

Although the present invention has been described in connection with the above exemplary embodiments, it will be appreciated by those skilled in the art that additions, deletions, modifications, and substitutions not specifically described may be made without department from the spirit and scope of the invention as defined in the appended claims.

The foregoing description is provided to enable a person skilled in the art to practice the various configurations described herein. While the subject technology has been particularly described with reference to the various figures and configurations, it should be understood that these are for illustration purposes only and should not be taken as limiting the scope of the subject technology.

There may be many other ways to implement the subject technology. Various functions and elements described herein may be partitioned differently from those shown without departing from the scope of the subject technology. Various modifications to these configurations will be readily apparent to those skilled in the art, and generic principles defined herein may be applied to other configurations. Thus, many changes and modifications may be made to the subject technology, by one having ordinary skill in the art, without departing from the scope of the subject technology.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

In some embodiments, any of the clauses herein may depend from any one of the independent clauses or any one of the dependent clauses. In one aspect, any of the clauses (e.g., dependent or independent clauses) may be combined with any other one or more clauses (e.g., dependent or independent clauses). In one aspect, a claim may include some or all of the words (e.g., steps, operations, means or components) recited in a clause, a sentence, a phrase or a paragraph. In one aspect, a claim may include some or all of the words recited in one or more clauses, sentences, phrases or paragraphs. In one aspect, some of the words in each of the clauses, sentences, phrases or paragraphs may be removed. In one aspect, additional words or elements may be added to a clause, a sentence, a phrase or a paragraph. In one aspect, the subject technology may be implemented without utilizing some of the components, elements, functions or operations described herein. In one aspect, the subject technology may be implemented utilizing additional components, elements, functions or operations.

The singular forms "a," "an," and "the" include plural referents unless the context clearly dictates otherwise. Thus, for example, reference to "a plunger component" includes reference to one or more plunger components, and reference to "the magnet" includes reference to one or more magnets.

In one or more aspects, the terms "about," "substantially," and "approximately" may provide an industry-accepted tolerance for their corresponding terms and/or relativity between items, such as from less than one percent to five percent.

As used herein, the term "substantially" refers to the complete or nearly complete extent or degree of an action, characteristic, property, state, structure, item, or result.

It is to be understood that a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 0.5 to 10 cm" should be interpreted to include not only the explicitly recited values of about 0.5 cm to about 10.0 cm, but also include individual values and sub-ranges within the indicated range. Thus, included in this numerical range are individual values such as 2, 5, and 7, and sub-ranges such as from 2 to 8, 4 to 6, etc. This same principle applies to ranges reciting only one numerical value. Furthermore, such an interpretation should apply regardless of the breadth of the range or the characteristics being described.

Unless otherwise defined, all technical and scientific terms used herein have the same meaning as commonly understood to one of ordinary skill in the art to which this disclosure belongs. Although any methods, devices and materials similar or equivalent to those described herein can be used in the practice or testing of the disclosure, representative methods, devices, and materials are described below.

A reference to an element in the singular is not intended to mean "one and only one" unless specifically stated, but rather "one or more." Pronouns in the masculine (e.g., his) include the feminine and neuter gender (e.g., her and its) and vice versa. The term "some" refers to one or more. Underlined and/or italicized headings and subheadings are used for convenience only, do not limit the subject technology, and are not referred to in connection with the interpretation of the description of the subject technology. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

The techniques described herein may be implemented in hardware, software, firmware, or any combination thereof, unless specifically described as being implemented in a specific manner. Any features described as modules or components may also be implemented together in an integrated logic device or separately as discrete but interoperable logic devices. If implemented in software, the techniques may be realized at least in part by a non-transitory processor-readable storage medium comprising instructions that, when executed, performs one or more of the methods described above.

The non-transitory processor-readable storage medium may comprise random access memory (RAM) such as synchronous dynamic random access memory (SDRAM), read only memory (ROM), non-volatile random access memory (NVRAM), electrically erasable programmable read-only memory (EEPROM), FLASH memory, other known storage media, and the like. The techniques additionally, or alternatively, may be realized at least in part by a processor-readable communication medium that carries or communicates code in the form of instructions or data structures and that can be accessed, read, and/or executed by a computer or other processor. For example, a carrier wave may be employed to carry computer-readable electronic data such as those used in transmitting and receiving electronic mail or in accessing a network such as the Internet or a local area network (LAN). Many modifications may be made to this configuration without departing from the scope or spirit of the claimed subject matter.

Although the detailed description contains many specifics, these should not be construed as limiting the scope of the subject technology but merely as illustrating different examples and aspects of the subject technology. It should be appreciated that the scope of the subject technology includes some embodiments not discussed in detail above. Various other modifications, changes and variations may be made in the arrangement, operation and details of the method and apparatus of the subject technology disclosed herein without departing from the scope of the present disclosure. Unless otherwise expressed, reference to an element in the singular is not intended to mean "one and only one" unless explicitly stated, but rather is meant to mean "one or more." In addition, it is not necessary for a device or method to address every problem that is solvable (or possess every advantage that is achievable) by different embodiments of the disclosure in order to be encompassed within the scope of the disclosure. The use herein of "can" and derivatives thereof shall be understood in the sense of "possibly" or "optionally" as opposed to an affirmative capability.

What is claimed is:

1. A method of operating a medical device for ultrasonic treatment, the method comprising:
controlling a supply of an electric energy to an ultrasonic instrument having a vibration transmission member that vibrates ultrasonically;
obtaining a temperature value, wherein the temperature value is a temperature increase rate of the vibration transmission member per unit time;
detecting a first peak at which the temperature increase rate changes from generally increasing to generally decreasing; and
controlling a power source to reduce or stop the supply of the electric energy to the ultrasonic instrument if a period in which the temperature increase rate decreases after the first peak is longer than a threshold value, wherein the power source is configured to supply the electric energy to the ultrasonic instrument.

2. The method of claim 1, further comprising determining completion of a cut of a living tissue based on the temperature increase rate.

3. The method of claim 1, further comprising:
detecting a minimum value of the temperature increase rate,
wherein controlling the power source to reduce or stop the supply of the electric energy to the ultrasonic instrument is based on the minimum value.

4. The method of claim 1, further comprising:
obtaining an integrated value of a temperature of the vibration transmission member,
wherein controlling the power source to reduce or stop the supply of the electric energy to the ultrasonic instrument is based on the integrated value.

5. The method of claim 1, further comprising:
obtaining an ultrasonic impedance value; and
detecting a second peak at which the ultrasonic impedance value changes from generally increasing to generally decreasing,
wherein controlling the power source to reduce or stop the supply of the electric energy to the ultrasonic instrument is based on the change of the ultrasonic impedance value and the second peak.

6. The method of claim 1, wherein the medical device includes the ultrasonic instrument, the power source, and a processor comprising a control unit operably connected to the power source.

7. A method of operating a medical device for ultrasonic treatment, the method comprising:
calculating a plurality of temperature rate change values corresponding to a temperature increase rate per unit time, based on a temperature of a vibration transmission member of an ultrasonic instrument of the medical device;
identifying a peak value among the plurality of temperature rate change values, the peak value being a largest value among the plurality of temperature rate change values;
determining whether the peak value is a false peak corresponding to an incomplete cut of living tissue or a true peak corresponding to a complete cut of living tissue;
when it is determined that the peak value is the false peak, then controlling a power source to reduce or stop providing power to an ultrasonic oscillator circuit for providing ultrasonic vibration to the vibration transmission member; and
when it is determined that the peak value is the true peak, then controlling the power source to continue providing power to the ultrasonic oscillator circuit.

8. The method of claim 7, wherein, if the peak value is smaller than a temperature rate change threshold value, then determining the peak value to be the false peak.

9. The method of claim 7, wherein, if the peak value is larger than a temperature rate change threshold value, then determining the peak value to be the true peak.

10. The method of claim 7, further comprising:
determining a plurality of ultrasonic impedance values corresponding to an ultrasonic impedance of the vibration transmission member, wherein the ultrasonic impedance of the vibration transmission member is based on the power supplied to the vibration transmission member;
identifying a first ultrasonic impedance value among the plurality of ultrasonic impedance values, the first ultrasonic impedance value being a largest value among the plurality of ultrasonic impedance values; and
determining that the first ultrasonic impedance value corresponds to the peak value.

11. The method of claim 7, further comprising:
calculating an integrated temperature value by integrating the temperature of the vibration transmission member;
determining that the integrated temperature value is greater than an integrated temperature threshold value;
when it is determined that the integrated temperature value is greater than the integrated temperature threshold value, then controlling the power source to reduce or stop providing power to the ultrasonic oscillator circuit; and
when it is determined that the integrated temperature value is greater than the integrated temperature threshold value, then controlling the power source to continue providing power to the ultrasonic oscillator circuit.

12. The method of claim 7, wherein the medical device includes the ultrasonic instrument having the vibration transmission member, the power source, and a processor comprising a control unit operably connected to the power source.

13. A medical control device, comprising:
a processor comprising a control unit operably connected to a power source, the control unit being configured to:
control a supply of an electric energy to an ultrasonic instrument,
obtain a temperature value, wherein the temperature value is a temperature increase rate of a vibration transmission member of the ultrasonic instrument per unit time,
detect a peak value at which the temperature increase rate changes from generally increasing to generally decreasing, and
control the power source to reduce or stop the supply of the electric energy to the ultrasonic instrument if a period in which the temperature increase rate decreases after the peak value is longer than a threshold value.

14. The medical control device according to claim 13, further comprising:
the power source, wherein the power source is configured to:
connect to the ultrasonic instrument having the vibration transmission member that vibrates ultrasonically, and
supply the electric energy to the ultrasonic instrument.

15. The medical control device of claim 13, further comprising:
a generator operated by the processor comprising:
an ultrasonic oscillator circuit configured to provide an output of an ultrasonic oscillation signal to a hand piece,
an output current detection circuit configured to detect a current of the ultrasonic oscillation signal output by the ultrasonic oscillator circuit,
an output voltage detection circuit configured to detect a voltage of the ultrasonic oscillation signal output by the ultrasonic oscillator circuit,
a first analog-to-digital converter (ADC) configured to convert an analog current value from the output current detection circuit to a digital current value,
a second ADC configured to convert an analog voltage value from the output voltage detection circuit to a digital voltage value; and
an integrated circuit configured to control the ultrasonic oscillator circuit of the generator, the integrated circuit comprising:
an impedance calculation block configured to calculate an impedance value, based on:
the digital current value from the first ADC, and
the digital voltage value from the second ADC,
a power calculation block configured to calculate an amount of power that has been supplied by the ultrasonic oscillator circuit, based on:
the digital current value from the first ADC, and
the digital voltage value from the second ADC,
a frequency detection block configured to detect a vibration frequency of the medical control device, based on:
the digital current value from the first ADC, and
the digital voltage value from the second ADC,
a temperature (t)/increase rate of T estimation block configured to determine an increase from a minimum of the temperature increase rate of the vibration transmission member, based on:
the calculated amount of power from the power calculation block, and
the detected vibration frequency from the frequency detection block, and
an output control block configured to control the output of the ultrasonic oscillation signal of the ultrasonic oscillator circuit of the generator, based on:
the digital current value from the first ADC,
the digital voltage value from the second ADC,
the calculated impedance value from the impedance calculation block, and
the determined increase from the minimum of the temperature increase rate of the vibration transmission member from the temperature (t)/increase rate of T estimation block,
wherein:
the temperature (t)/increase rate of T estimation block is further configured to detect a minimum value and the peak value of the temperature increase rate, and
the increase from the minimum of the temperature increase rate of the vibration transmission member is a difference between the peak value and the minimum value.

16. The medical control device of claim 15, wherein the temperature (t)/increase rate of T estimation block is further configured to:
determine whether the peak value is a false peak corresponding to an incomplete cut of living tissue or a true peak corresponding to a complete cut of living tissue,
when it is determined that the peak value is the false peak, then the output control block is further configured to control the ultrasonic oscillator circuit to stop or reduce the output of the ultrasonic oscillation signal, and
when it is determined that the peak value is the true peak, then the output control block is further configured to control the ultrasonic oscillator circuit to maintain the output of the ultrasonic oscillation signal.

17. The medical control device of claim 16, wherein, if the increase is smaller than a temperature rate change threshold value, then the temperature (t)/increase rate of T estimation block is further configured to determine the peak value to be the false peak.

18. An ultrasonic treatment system, comprising the medical control device of claim 13, further comprising:
a controller comprising an input controller comprising:
the processor, and
an actuation switch; and
a treatment instrument comprising:
a treatment section comprising an end-effector configured to grasp living tissue to perform treatment, a grip connected to the controller via a cable, the grip comprising:
an opening/closing actuator configured to operate opening and closing of the treatment section, the opening/closing actuator being arranged at one end of the grip and configured to transmit operation of the opening/closing actuator to the treatment section, and
a grasping portion configured to be grasped when the treatment instrument is operated, and
a shaft.

19. The ultrasonic treatment system of claim 18, wherein:
the shaft extends into the grip and comprises:
an internal portion inside the grip, and
an external portion outside of the grip,
the internal portion of the shaft comprises:
an internal shaft, and
a slider configured to contribute to longitudinal movement of the internal shaft, and
a force sensor is disposed at an end of the slider, the force sensor being configured to detect a strain value, the strain value being a stress in a long axis direction generated by longitudinal movement of the shaft, while the power source is providing the supply of the electric energy for ultrasonic vibration.

20. The ultrasonic treatment system of claim 19, wherein:
the strain value detected by the force sensor is proportional to a gripping force of the user, such that a higher strain value corresponds to the user's squeezing the opening/closing actuator harder, and
the processor is further configured to reduce or stop the power source from providing the supply of the electric energy for ultrasonic vibration if a change in the value of the strain sensor exceeds a strain threshold value.

* * * * *